United States Patent [19]

Reichenberger

[11] 4,148,305

[45] Apr. 10, 1979

[54] CATHODE FOR POLAROGRAPHIC MEASUREMENTS IN PHYSIOLOGICAL MEDIUM

[75] Inventor: Helmut Reichenberger, Brand, Fed. Rep. of Germany

[73] Assignee: Siemens Aktiengesellschaft, Berlin & Munich, Fed. Rep. of Germany

[21] Appl. No.: 773,603

[22] Filed: Mar. 2, 1977

[30] Foreign Application Priority Data

Mar. 29, 1976 [DE] Fed. Rep. of Germany ....... 2613355

[51] Int. Cl.$^2$ .......................... A61B 5/00; A61B 5/05
[52] U.S. Cl. ................................. 128/2 E; 204/195 P
[58] Field of Search ............................ 128/2 E, 2.1 E; 204/195 P, 195 B, 1 P

[56] References Cited

U.S. PATENT DOCUMENTS

| 3,399,667 | 9/1968 | Nishimoto et al. | 128/2 E |
|---|---|---|---|
| 3,719,575 | 3/1973 | Niedrach et al. | 204/195 P |
| 3,749,089 | 10/1971 | Derr | 128/2.1 E |
| 3,912,614 | 10/1975 | Spracklen | 204/195 P |

OTHER PUBLICATIONS

Shinmaru, S., "Cathether-Mounted Oxygen Electrode for Monitoring Oxygen Tension", In Cardiovascular Research Center Bulletin, Apr.-Jun. 1972, pp. 111-122.
Chandler, M.T., Stationary Platinum Electrode for Measurement of $O_2$ Exchange by Biological Systems Under Hydrostatic Pressure, In the Review of Scientific Instruments, 42 (i): pp. 143-146, Jan. 1971.

Primary Examiner—Robert W. Michell
Assistant Examiner—Arthur S. Rose
Attorney, Agent, or Firm—Hill, Gross, Simpson, Van Santen, Steadman, Chiara & Simpson

[57] ABSTRACT

A cathode for polarographic measurements in physiological medium, such as measuring oxygen partial pressure in a human or animal body, is comprised of an elongated cable having a conductive filament, such as a steel wire or a carbon fiber enveloped within an insulating material, such as a layer of polyurethane and sheated in a body-tolerable insulating material, such as a layer of polytetrafluoroethylene. The proximal end of the conductive filament is coated with a layer of a precious metal, such as gold or platinum, and the front face of the cable is provided with a layer of an oxygen-permeable electrically conductive membrane, such as composed of polymethylacrylate or polystyrene. The distal end of the conductive filament is connected to an electrical source, a signal display means and/or a signal processing means.

10 Claims, 1 Drawing Figure

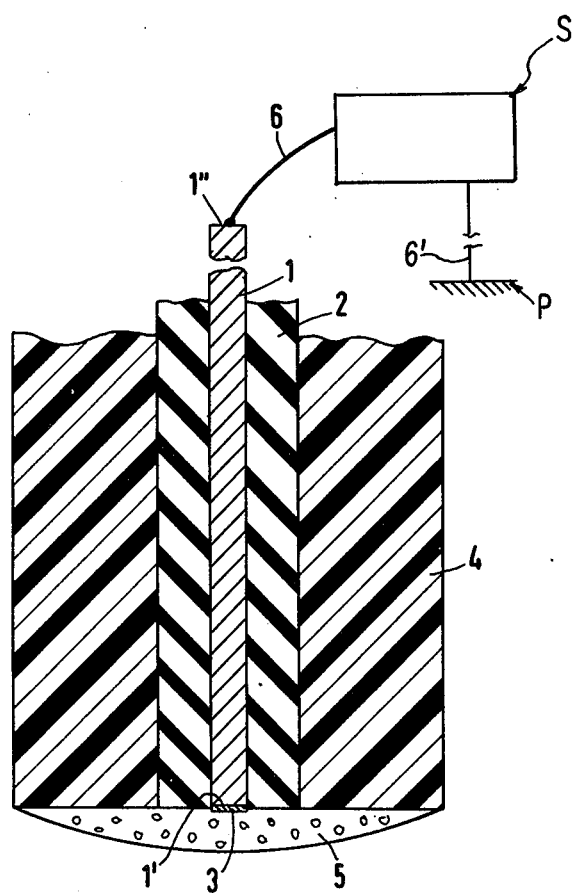

CATHODE FOR POLAROGRAPHIC MEASUREMENTS IN PHYSIOLOGICAL MEDIUM

BACKGROUND OF THE INVENTION

1. Field of the Invention

The invention relates to cathode structures and somewhat more particularly to polarographic cathode structures useful in physiological mediums.

2. Prior Art

S. Sinmaru et al. in an article entitled "Catheter-Mounted Oxygen Electrode For Monitoring Oxygen Tension", appearing in "Cardiovascular Research Center Bulletin", April–June 1972, page 112, describe a cathode for polarographic measurements comprised of a steel wire having a piece of a gold wire attached to the proximal tip of the steel wire. The steel wire with the attached gold wire is coated or sealed within an insulating material and this insulating envelope is further sheathed in a layer of a body-tolerable material. The proximal tip of the gold wire is covered with an oxygen-permeable membrane and contacts the physiological medium. The manufacture of this type of polarographic cathode structure is complicated. Each steel wire piece must be individually connected to a gold wire piece, for example, by spot welding. Accordingly, such cathodes are comparatively expensive.

Another known polarographic cathode structure is comprised of a cable section having at least one continuous strand of a precious-metal wire therein, preferably a gold wire, which is enveloped in an insulating material. In the manufacture of this type of cathode structure, cut sections or pieces of an insulated precious metal cable are utilized. Cathode structures of this type have proven successful for polarographic measurement in physiological medium. The manufacture of this type of cathode structure is relatively simple. However, because of the need for continuous gold wires, these cathodes are relatively expensive. Economical considerations play a major role in the use of such cathodes which, for medical reasons, are preferably developed as throw-away articles or as articles of one-time use. Further, gold wires having small diameters are mechanically weak so that special care is required during the manufacture and handling of cathodes containing such gold wires.

SUMMARY OF THE INVENTION

The invention provides a polarographic cathode structure for use in physiological medium and which avoids or at least minimizes the above prior art drawbacks.

Cathodes constructed in accordance with the principles of the invention function to measure polarographic data in physiological medium at least as well as the prior art structures but are substantially more economical and may be employed as throw-away articles which have adequate mechanical properties for problem-free handling.

In accordance with the principles of the invention, a cathode structure is comprised of a continuous filament composed of a conductive non-precious material, such as steel or carbon, having a front end face thereof coated with a thin layer of a precious metal, such as gold or platinum and which is enveloped in an insulating material. The precious metal layer may be applied, for example, to the frontal end face of a steel wire by a controlled electrolytic deposition process so that a select layer thickness is readily achieved. Further, a plurality of conductive filaments or wires may be simultaneously provided with, for example, a gold layer via the electrolytic deposition process for improved economy.

BRIEF DESCRIPTION OF THE DRAWING

The drawing illustrates an elevated and somewhat schematic cross-sectional view, partially broken away, of a cathode constructed in accordance with the principles of the invention.

DESCRIPTION OF THE PREFERRED EMBODIMENTS

The invention provides a cathode for polarographic measurement in physiological medium, such as for measuring oxygen partial pressure in human or animal bodies as well as a method of manufacturing such cathodes.

Cathodes constructed in accordance with the principles of the invention may be operationally coupled at their distal end via an operational circuit to an electrical source and to a signal display means and/or a signal processing means. The proximal end of such cathodes may be covered with an oxygen-permeable electrically conductive membrane and many be operationally connected to an anode via the physiological medium.

As shown on the drawing, a cathode construction in accordance with the principles of the invention may be comprised of an elongated (basically round) conductive cable piece or section having an elongated conductor or wire 1 which includes a proximal end 1' and a distal end 1'' and is enveloped by an insulating envelope 2, which is absent from the distal and proximal ends of the conductor. The filament or wire 1 is composed of a common or non-precious conductive material, such as steel or carbon and has a diameter in the order of magnitude of about 10 to 100 $\mu$m and, in an exemplary embodiment has a preferred diameter of about 60 $\mu$m. The insulating envelope 2 may be composed of a suitable dielectric lacquer-like material, for example, polyurethane. The fragmentary components of the basic cable may comprise select length pieces or sections cut from longer, for example, steel wire, insulated cables (commercially available in any desired lengths) which may be continuously manufactured in a conventional manner.

A relatively thin layer 3 composed of a precious or noble metal is applied onto the front surface of the proximal end 1' of filament 1. The layer 3 is composed, for example, of gold or platinum or some other noble metal and preferably has a thickness of several micrometers. The precious metal layer 3 may be applied in a controlled manner, for example, by an electrolytic deposition process and may be simultaneously applied to a large number of suitable cable sections.

The basic cable section, comprised of elements 1 and 2 having a thin, for example, gold layer 3 on a front end face of element 1, is provided with an external sheathing 4 composed of a body-tolerable material, such as polytetrafluoroethylene.

An oxygen-permeable electrically conductive membrane 5 is applied over the entire proximal end of the cathode as shown. The membrane 5 may be applied, for example, by dipping or immersing a gold-coated steel wire proximal end into a bath composed of a material forming the membrane. Preferably, the membrane is composed of materials which are hydrophilic and only porous to relatively small molecules and/or ions but non-porous to macromolecules, such as proteins. Preferably, the membrane 5 is composed of a material selected from the group consisting of cross-linked polymethylacrylate, polystyrene and cellulose acetate.

The distal end 1" of filament 1 is operationally coupled (for example, by soldering or via a suitable connector of sleeve) via an electrical lead 6 to a means S which provides an electrical potential to the cathode from a suitable electrical source and which measures, displays or otherwise processes the polarographic signals received from the cathode. Means S is shown as being provided with another electrical lead 6' which may be coupled to the patient P via an anode so as to complete an operational electrical circuit.

As indicated earlier, other combinations of a wire or filament composed of a non-precious electrically conductive material having a layer of a precious metal applied onto a proximal front end face of the wire may also be utilized in constructing cathodes in accordance with the principles of the invention. An exemplary embodiment of such other combination is a carbon fiber coated at an end face thereof with platinum.

The savings in material cost of previous metal and the savings in manufacturing costs realized by constructing cathodes in accordance with the principles of the invention are considerable relative to prior art cathodes, such as discussed earlier. Further, the mechanical stability or strength during manufacturing and/or handling of cathodes having a construction in accordance with the principles of the invention is good.

The method embodiments of the invention generally comprise (1) providing a select length of an elongated conductive cable having an insulating envelope about an electrically conductive filament having at least one end face thereof free of the insulating envelope; (2) coating a thin layer of a precious metal onto the end face of the conductive filament; (3) applying a layer of a body-tolerable material about only the insulating envelope; and (4) applying a layer of an oxygen-permeable conductive material onto the entire end portion of the resultant structure, i.e., a so-coated filament end, adjacent insulating envelope end surface and the adjacent end surface of the layer composed of the body-tolerable layer. In certain embodiments, the initially provided cable may include an outer layer of a body-tolerable material about the insulating layer so that step (3) may be omitted and/or combined with step (1).

In a preferred method, the first step of the method may comprise cutting or otherwise severing a plurality of individual select length cables from a suitable cable supply, as a reel having an unlimited length of suitable cable thereon. In this manner, any number of select length cable pieces may be simultaneously produced for improved manufacturing efficiency.

In a preferred method, the second step of method may comprise applying the thin layer of a precious metal onto an end face of the conductive filament via a controlled electrolytic deposition process. For example, a plurality of select length cable pieces having an uncovered filament end may be positioned within a suitable electrolytic bath and a thin layer of a precious metal be electrolytically deposited or plated onto each filament end.

In like fashion, the body-tolerable material may be simultaneously applied to a plurality of cable sections or pieces in instances where the initial cable lacks a layer of such material.

In a preferred method, the fourth step of the method may comprise applying the layer of oxygen-permeable conductive material onto the end of the cable having a layer of precious or noble metal on the filament end thereof via dipping or immersing one or a plurality of, for example, gold-coated ends of steel wire, into a bath containing an oxygen-permeable conductive material, which preferably is selected from the group consisting of cross-linked polymethylacrylate, polystyrene and cellulose acetate.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

I claim as my invention:

1. In a cathode for polarographic measurements in physiological medium, such as for measuring oxygen partial pressure in a human or animal body, comprised of an elongated insulated conductive cable, having a distal end thereof operationally connected to an electrical source and a signal display or processing means, and having a proximal end thereof covered with an oxygen-permeable electrically conductive membrane and operationally connected with an anode via a physiological medium; the improvement comprising:
   wherein said conductive cable has an elongated substantially round filament therein comprised of an electrically conductive non-precious material, said filament having a definite diameter dimension less than that of said conductive cable, and
   a relatively thin layer of a precious metal coating positioned directly on a proximal end face of said filament, said precious metal thin layer having a diameter dimension substantially equal to that of said filament.

2. In a cathode as defined in claim 1 wherein said filament is composed of a material selected from the group consisting of steel and carbon and said precious metal is selected from the group consisting of gold and platinum.

3. In a cathode as defined in claim 1 wherein said oxygen-permeable electrically conductive membrane is composed of a material selected from the group consisting of cross-linked polymethylacrylate, polystyrene and cellulose acetate.

4. In a cathode as defined in claim 1 wherein said definite diameter dimension of said filament is in a range from about 10 to about 100 micrometers.

5. A cathode for polarographic measurements in physiological medium, such as for measuring oxygen partial pressure in a human or animal body, comprising:
   an elongated electrically conductive filament having a distal end and a proximal end, said filament having a definite diameter and being composed of an electrically conductive non-precious material;
   a relatively thin layer coating composed of a precious metal positioned directly on only a proximal end face of said filament, said precious metal coating having a diameter dimension substantially equal to that of said filament;
   an insulating envelope about said filament and absent from the distal and proximal ends thereof;
   an external sheathing composed of a body-tolerable material about said insulating envelope; and an oxygen-permeable electrically conductive membrane on at least a free face of said thin layer of precious metal.

6. A cathode as defined in claim 5 wherein said conductive filament is composed of a material selected from the group consisting of steel and carbon.

7. A cathode as defined in claim 5 wherein said precious metal is selected from the group consisting of gold and platinum.

8. A cathode as defined in claim 5 wherein said oxygen-permeable membrane is composed of a material selected from the group consisting of cross-linked polymethylacrylate, polystyrene and cellulose acetate.

9. A cathode as defined in claim 5 including means for supplying an electrical potential to said cathode and for displaying and processing signals received from said cathode.

10. A cathode as defined in claim 5 wherein said definite diameter of the filament is in the range of about 10 to about 100 micrometers.

* * * * *